United States Patent [19]

Chabardes et al.

[11] 4,433,171

[45] * Feb. 21, 1984

[54] SULPHONES HAVING A 1,5-DIMETHYL-HEXA-1,5-DIENYLENE GROUP

[75] Inventors: Pierre Chabardes, Sainte Foy-les-Lyon; Marc Julia, Paris; Albert Menet, Colmar, all of France

[73] Assignee: Rhone-Poulenc S.A., Paris, France

[*] Notice: The portion of the term of this patent subsequent to May 25, 1999 has been disclaimed.

[21] Appl. No.: 345,748

[22] Filed: Feb. 4, 1982

Related U.S. Application Data

[60] Division of Ser. No. 759,474, Jan. 14, 1977, abandoned, which is a continuation-in-part of Ser. No. 328,537, Feb. 1, 1973, Pat. No. 4,331,814.

[30] Foreign Application Priority Data

Feb. 2, 1972 [FR] France .................. 72.03482
Apr. 10, 1972 [FR] France .................. 72.12477

[51] Int. Cl.³ .......................................... C07C 147/06
[52] U.S. Cl. .................................... 568/33; 560/255; 568/31; 568/32
[58] Field of Search .................... 568/31, 32, 33; 560/255

[56] References Cited

U.S. PATENT DOCUMENTS 3,075,003  1/1963  Blumenthal .................. 260/488
3,665,040  5/1972  Ruegg et al. .................. 424/331
3,850,991  11/1974  Chabardes et al. .................. 568/32
3,960,967  6/1976  Olson et al. .................. 260/563 R
4,110,538  8/1978  Decôr .................. 568/32
4,331,814  5/1982  Chabardes et al. .................. 568/31

*Primary Examiner*—Donald G. Daus
*Assistant Examiner*—M. C. Eakin
*Attorney, Agent, or Firm*—Stevens, Davis, Miller & Mosher

[57] ABSTRACT

Sulphones useful for preparing polyenes have the formula:

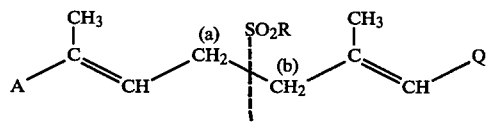

where the sulphonyl group replaces a hydrogen atom on carbon atom (a) or (b), R represents alkyl, aralkyl or aryl, optionally substituted, A and Q represent an optionally substituted hydrocarbon of 5n+1 carbon atoms (n is 1-5), methyl, optionally substituted by halogen, sulphide or sulphone, $CH_2OH$ (or an ether or ester thereof), CHO (optionally protected), COOH (or an acid chloride, ester or nitrile thereof), with the proviso that when A represents a 2-(2,6,6-trimethylcyclohex-1-enyl) ethenyl radical, Q cannot represent —COOH or an ester thereof.

5 Claims, No Drawings

SULPHONES HAVING A 1,5-DIMETHYL-HEXA-1,5-DIENYLENE GROUP

This is a division of application Ser. No. 759,474, filed Jan. 14, 1977, now abandoned, which in turn is a continuation-in-part of application Ser. No. 328,537, filed Feb. 1, 1973, now U.S. Pat. No. 4,331,814.

This invention relates to sulphones having a 1,5-dimethylhexa-1,5-dienylene group and their applications as intermediates in organic synthesis.

The present invention provides a sulphone corresponding to the general formula:

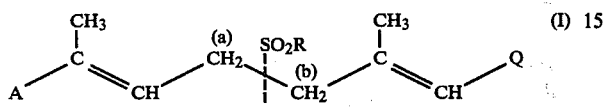

in which the sulphonyl group —$SO_2R$ replaces a hydrogen atom on carbon atom (a) or (b), R represents an alkyl, e.g., of 1 to 4 carbon atoms, aralkyl or aryl radical, each of which is substituted or unsubstituted, each of A and Q, which may be the same or different, represents (a) a hydrocarbon radical containing 5n+1 carbon atoms (n being an integer of 1-5) which is substituted or unsubstituted.

(b) a methyl radical, which is unsubstituted or substituted by a halogen e.g. chlorine or bromine or by a —SR' or —$SO_2R'$ group in which R' represents an alkyl, aralkyl or aryl radical, which is substituted or unsubstituted, (c) a primary alcohol group —$CH_2OH$, an ether group thereof or an ester which it forms with an inorganic or organic acid, (d) a free or protected aldehyde group, (e) an acid group —COOH, its acid chloride group, an ester thereof or a nitrile group with the proviso that, when A represents a 2-(2,6,6-trimethyl-cyclohex-1-enyl)ethenyl radical, Q cannot represent —COOH or an ester thereof.

When A or Q represents a hydrocarbon radical containing 5n+1 carbon atoms, this radical can be saturated or unsaturated and with conjugated and/or unconjugated ethylenic unsaturation, this radical can possess functional groups or it can be substituted by alkyl groups; when n is 2 to 5, this radical can contain a ring to which alkyl groups and/or functional groups such as O= or —OH may be attached, the functional groups being free or protected.

R and R' preferably represent aryl radicals, e.g. aromatic hydrocarbon radicals (such as phenyl or naphthyl radicals) which may optionally be substituted by one or two radicals such as halogen, e.g. fluorine, chlorine or bromine, alkyl of preferably 1 to 4 carbon atoms, e.g., methy, or alkoxy of 1 to 4 carbon atoms, e.g. methoxy.

The hydrocarbon radical represented by A or Q preferably is a group having a carbon skeleton of formula:

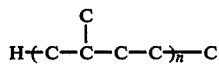

wherein n is 1-5, each $C_5$ unit containing 0-2 ethylenic double bonds, the remaining valencies being satisfied by hydrogen atoms, or two adjacent $C_5$ units are joined to form a structure containing a ring of 6 ring carbon atoms, which can be substituted by a hydroxy or oxo groups, by a methyl group additional to the methyl substituents forming part of the carbon skeleton of $C_5$ units, and the chain of $C_5$ units can have one substituent of formula $SO_2R$, wherein R is as defined above, in a grouping

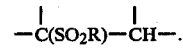

The ring is usually a 2,6,6-trimethylcyclohex-1-enyl ring.

A preferably represents a 2-(2,6,6-trimethylcyclohex-1-enyl)-ethenyl, a 6-(2,6,6-trimethylcyclohex-1-enyl)-4-methylhexa-1,3,5-trienyl, 4-methylpent-3-enyl, 4,8-dimethylnona-3,7-dienyl, methyl or t-butoxymethyl radical. A can also preferably represent a saturated or unsaturated linear or branched chain alkyl radical (within the broad definition given for A above) or a 2-(2,6,6-trimethyl-3-oxo-cyclohex-1-enyl)-ethenyl group.

Q represents a COOH or CN group carboxylic acid alkyl ester group of 2 to 7 carbon atoms, a $CH_2OH$ group or an alkyl ether group thereof containing a total of 2 to 7 carbon atoms or an ester group thereof with an alkanoic acid of 1 to 6 carbon atoms, a CHO group or dialkyl acetal with 1 to 6 carbon atoms in each alkyl group, or a sulphone group of formula $CH_2SO_2R'$ or a polyene radical containing a 2,6,6-trimethylcyclohex-1-ene ring. Preferred radicals for Q are an acetoxymethyl, hydroxymethyl, methoxymethyl, t-butoxymethyl, diethoxymethyl, phenylsulphonylmethyl, 6-(2,6,6-trimethylcyclohex-1-enyl)-4-methyl-1 or 2-phenylsulphonylhexa-3,5-dienyl radical or a 10-(2,6,6-trimethylcyclohex-1-enyl)-4,8-dimethyl-2-phenylsulphonyl deca-3,5,7,9-tetraenyl radical.

A may also represent any of the radicals listed above for Q and vice versa, subject to the proviso clause above.

The present invention also provides a process for preparing a sulphone of formula I which comprises reacting a compound of the formula A—$C(CH_3)$=CH—$CH_2X$ with a compound of the formula Q—CH=$C(CH_3)$—$CH_2Y$ one of X and Y representing a halogen and the other $SO_2R$, in the presence of a basic agent capable of converting the compound, in which X or Y represents a $SO_2R$ group, into an anion, A, Q and R being as defined above. This process has two embodiments. In this first embodiment for the preparation of the sulphones of formula I, in which the sulphonyl group replaces a hydrogen atom on carbon atom (a) the process comprises reacting a sulphone of the formula A—$C(CH_3)$=CH—$CH_2SO_2R$ (XVII) with a halide of the formula Q—CH=$C(CH_3)$—$CH_2X$, in the presence of a basic agent, capable of converting the sulphone XVII into its anion, A, Q and R being as defined above and X representing a halogen atom, and in particular chlorine or bromine. An equation for the reaction can be given as follows.

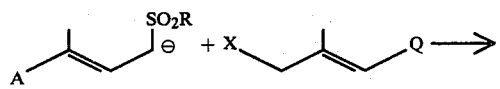

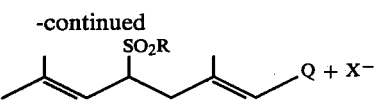

In the second embodiment, a halide of the formula A—C(CH$_3$)=CH—CH$_2$X and a sulphone Q—CH=C(CH$_3$)—CH$_2$SO$_2$R are reacted together in the presence of the basic agent to obtain a compound in which the —SO$_2$R group replaces a hydrogen atom on carbon atom (b), as shown below:

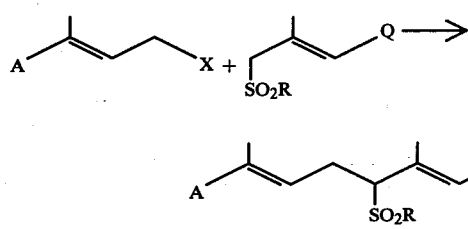

The reaction is carried out in the presence of a basic agent which possesses sufficient activity to convert the sulphone employed into an anion. The basic agents which are suitable are inorganic or organic compounds, examples of which are alkali metal alcoholates, alkali metal hydrides or amides and organometallic compounds such as organo-zinc, organo-lithium and organo-magnesium compounds. They can be used alone or in conjunction with another basic agent intended to neutralise the hydrohalic acid formed. When the basic agent is used alone, the amount employed must be sufficient to achieve this neutralisation. The amount used also depends on how the reaction is carried out and on the reactivity of the products of the reaction with respect to this basic agent. For these various reasons, it can be advantageous to employ a smaller amount of basic agent in the reaction and to add another basic agent, with respect to which the products of the reaction are less sensitive in an amount sufficient to neutralise the hydrohalic acid formed.

The reaction can be carried out at temperatures which can range from −100° C. to +150° C., depending on the nature of the products employed and produced.

In order that the reaction can take place satisfactorily, it is advantageous to carry it out in an organic solvent which can be a hydrocarbon such as hexane, benzene or toluene, a protic solvent, e.g. methanol, ethanol or ethylene glycol, or a linear or cyclic ether of a monoalcohol or a diol such as diethyl ether, dioxane or tetrahydrofuran. Other solvents such as dimethylformamide, dimethylacetamide, dimethylsulphoxide, N-methylpyrrolidone and hexamethylphosphotriamide are also suitable.

In certain cases, e.g. when A or Q represents a CH$_2$SO$_2$R' group, wherein R' is as defined above, the halogenated derivative reacting with the sulphone can be replaced by a compound which possesses a terminal conjugated diene chain, for example a compound of the formula Q'=CH—C(CH$_3$)=CH$_2$ in which Q' represents a divalent radical such that Q'H corresponds to Q as defined above. The reaction is then represented by the equation:

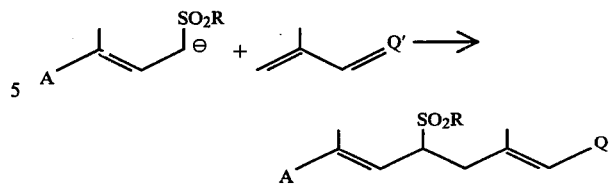

and it gives rise to the formation of a product with the sulphone group replacing a hydrogen atom on carbon atom (a), which is identical to that obtained by reacting the same sulphone with a halogenated derivative Q—CH=C(CH$_3$)—CH$_2$X.

If a sulphone of the formula Q—CH=C(CH$_3$)—CH$_2$SO$_2$R is reacted with a diene compound of the formula A'=C(CH$_3$)—CH=CH$_2$, in which A' represents a divalent radical such that A'H corresponds to A, a compound of formula I is obtained in which the sulphone group replaces a hydrogen atom on carbon atom (b), the reaction being represented by the following equation:

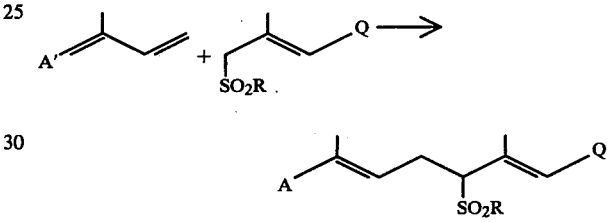

This condensation of diene compounds with a sulphone is carried out in the presence of an inorganic or organic alkaline agent such as an alkali metal hydroxide or alcoholate, an amine such as diethylamine, diisopropylamine, pyridine, triethylamine and tributylamine, or a quaternary ammonium hydroxide. The reaction can be carried out with or without a solvent, but it is however preferable to choose a solvent so that the reaction takes place in a homogeneous phase. This solvent can be an alcohol such as methanol, ethanol and tertiary butyl alcohol or an ether such as diethyl ether, dioxane and tetrahydrofuran or any other inert solvent such as benzene, toluene, dimethylformamide, or acetonitrile.

The reaction takes place at ambient temperature and when the reaction products are not affected by heating, the reaction can be accelerated by carrying it out at a higher temperature. If the reaction products are sensitive to heat, the reaction can be carried out at temperatures below ambient temperature. A description of all the working conditions relating to the Michael Reaction, of which this variant is an application, will be found in "Organic Reactions, vol. 10, p. 264–266—The Michael Reaction".

The sulphones used to prepare the products of the general formula I are known products or new products. They are generally obtained by reacting an alkali metal sulphinate of the formula RSO$_2$M, wherein M represents an alkali metal, with a halogenated compound in accordance with a usual method for preparing sulphones. In the case of those which are employed in the following Examples, their preparation will be given in these examples.

Compounds of formula A—C(CH$_3$)=CH—CH$_2$SO$_2$R and wherein A represents a 2-(2,6,6-trimethylcyclohex-1-enyl)ethylene group are described and claimed in U.S. Ser. No. 218,838 filed Jan. 18, 1972, now U.S. Pat. No. 3,781,313 by Marc Julia.

They may be prepared by reacting an alkali metal sulphinate of formula RSO$_2$M, wherein R and M are as defined above with either a compound of formula A—C(CH$_3$)=CH—CH$_2$X, wherein X represents chlorine, bromine or iodine, obtained by halogenation of vinyl-$\beta$-ionol with a phosphorus trihalide, or with vinyl-$\beta$-ionol itself.

Compounds of formula A—C(CH$_3$)=CH—CH$_2$SO$_2$R wherein A represents a group —CH$_2$X or CH$_2$SO$_2$R, where X represents a halogen, are described and claimed in U.S. Ser. No. 328,600 filed Feb. 1, 1973, now abandoned by Albert Menet. They may be prepared by reacting an akali metal sulphinate of formula RSO$_2$M with a 1,4-dihalogeno-2-methylbut-2-ene, or, when A represents a group CH$_2$SO$_2$R with a compound of formula X—C(CH$_3$)=CH—CH$_2$SO$_2$R, where X represents a halogen.

Compounds of formula A—C(CH$_3$)=CH—CH$_2$SO$_2$R and Q—CH=C(CH$_3$)—CH$_2$SO$_2$R, wherein A and Q represent a group CH$_2$OR$_1$ where R$_1$ represents an alkyl or aryl group which may be substituted, are described and claimed in U.S. Ser. No. 328,611 filed Feb. 1, 1973, now U.S. Pat. No. 3,835,195 by Albert Menet. They may be prepared by reacting an alkali metal compound of R$_1$OM with a 4-alkyl- (or aryl) sulphonyl- 2- or 3-methylbut-2-enyl halide.

Compounds of formula A—C(CH$_3$)=CH—CH$_2$—SO$_2$R in which A represents a 6-(2,6,6-trimethylcyclohex-1-enyl) 4-methylhexa-1,3,5-trienyl radical are described and claimed in U.S. Ser. No. 254,103 filed May 17, 1972, now U.S. Pat. No. 3,803,252 in the name of Pierre Chabardes and Marc Julia. They may be prepared by reacting an alkali metal sulphinate with retinol or a retinol ester of an inorganic or organic acid, e.g. retinyl chloride, or with 3-retinol.

Retinyl halides, which are known compounds are preferably prepared by a process comprising reacting 1-(or 3)-retinol with a halogenating reagent (e.g. phosphorus trichloride or tribromide) at a low temperature and in an inert solvent. This process is described and claimed in U.S. Ser. No. 254,102 filed May 17, 1972, now abandoned in the name of Pierre Chabardes.

The diene compounds employed in the variant of the process can be obtained, for example, by dehydrochlorination of a chlorinated compound by means of an inorganic or organic alkaline agent. The halides are products the majority of which are well known and their preparation will also be given in the Examples.

The sulphones of the formula I are used to prepare polyene compounds belonging to the series of terpenes, geraniolenes, sesquiterpenes and carotenes, and more generally they can be used to prepare any compound containing a polyisoprene chain with various degrees of saturation. By means of them, it is possible to synthesise these compounds from molecules which possess fewer carbon atoms, by adding to the latter one or more isoprene chains, which carry the functional group characteristic of the desired compounds. The addition of several isoprene units can be carried out in a single stage if a product containing the desired number of isoprene units is used, or in successive stages giving rise to the formation of several sulphone groups on the same molecule. Whatever the method of synthesis chosen, desulphonation of the product obtained can be carried out by a suitable reduction treatment e.g. with lithium and ethylamine and compounds containing one or more diene chains

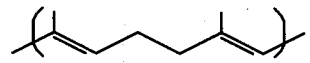

are then obtained. It can also be carried out by treatment with an inorganic or organic basic agent such as, an alkali metal hydroxide, an alkali metal carbonate or an alkali metal alcoholate, and compounds containing one or more conjugated triene chains

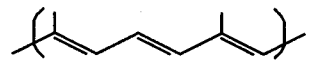

characteristic of polyisoprene compounds are obtained. Desulphonation of any

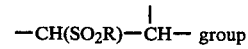

in the rest of the sulphone of formula I usually occurs with the reduction or elimination at carbon atoms (a) and (b).

Depending on the method of desulphonation chosen, it is possible to prepare compounds having the above diene or triene chains, for example, acyclic or cyclic, terpene products such as ocimene, geraniol, citronnellol, citral all of which are used in perfumes, geranic acid and its esters, farnesal, farnesol and its esters, farnesic acid and its derivatives, axerophthene and its lower or higher isoprene homologues and the functional derivatives of this same series, particularly retinal and its acetals, vitamin A, its ethers and its esters, vitamin-A-acid, its esters, its nitrile, other functional derivatives of retinene such as 4-oxo-retinal, apocarotenals and the corresponding alcohols as well as their ethers and their esters, apocarotenic acids and their derivatives. Carotenoid compounds containing 40 or more than 40 atoms can also be prepared, examples of which are the various carotenes such as $\beta$-carotene, a naturally occurring colorant, $\gamma$-carotene, lycopene, squalene, canthaxanthine, zeaxanthine, isozeaxanthine and more generally xanthophyllic compounds corresponding to these various carotenes. Such methods of synthesis employing sulphones of formula I can also be used to prepare compounds in which the molecule contains a saturated or unsaturated polyisoprene chain as in vitamin E or vitamines K$_1$ and K$_2$.

The desulphonation can be carried out on the sulphone isolated from the reaction medium or within this medium. Whatever the method chosen, it results in the liberation of an alkali metal sulphinate or a sulphinic acid which can be reused in the preparation of the starting sulphone, so that, since the synthesis of the polyisoprene compounds proceeds via these sulphones as intermediates, practically no alkali metal sulphinate is consumed.

The following Examples illustrate the preparation of sulphones according to the invention and their application in organic synthesis.

EXAMPLE 1

(a) 16.8 g. of potassium t-butylate (15×10$^{-2}$ mol) and 90 cm$^3$ of tetrahydrofuran are introduced into a 500 cm³ three-necked flask equipped with a magnetic stirrer, a condenser and a dropping funnel. The mixture is cooled to −30° C. and 25.7 g (7.5×10⁻² mol) of phenyl-5-(2,6,6-trimethyl-cyclohex-1-enyl)-3-methyl-penta-2,4-dienyl-sulphone diluted in 65 cm³ of tetrahydrofuran are run in, with stirring. The reaction mixture is left for 30 minutes at this temperature and then 14.5 g (8.9×10⁻² mol) of 1-chloro-2-methyl-4-acetoxy-2-butene in 25 cm³ of tetrahydrofuran are run in (duration of addition approximately 40 minutes). The reaction mixture is kept at −30° C. and at the end of 5 hours it is poured rapidly into 2 liters of a 50/50 water/diethyl ether mixture. After washing with water and drying the ether layer followed by evaporation in vacuo, 35.3 g of a red viscous mass are obtained, in which the products of the reaction are measured by thin layer chromatography (silica, hexane/diethyl ether in a volume ratio of 70/30). This determination indicates that 95% of the starting sulphone has been converted into the desired sulphone-ester (yield 65-70%) and into the corresponding sulphone-alcohol (20-25%) as a result of saponification of the ester.

Recrystallization of the crude product from methanol yields a white solid, of melting point 90° C., identified by elementary analysis, infra-red spectrography and nuclear magnetic resonance. When dissolved in ethanol, it gives an absorption maximum at 273 nm ($E_1\,_{cm}{}^{1\%}$=408) and at 248 nm ($E_1\,_{cm}{}^{1\%}$=360) in UV spectrography. It corresponds to the formula:

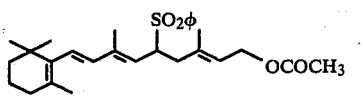
(II)

1-Chloro-2-methyl-4-acetoxy-2-butene was prepared in accordance with the process described in J. Am. Chem. Soc. 72 4610 (1950) by reacting t-butyl hypochlorite with isoprene in an acetic acid medium.

The starting sulphone is obtained by reacting an alkali metal phenylsulphinate with a halide of the same carbon structure. This sulphone and its preparation are described and claimed in our aforesaid Ser. No. 218,838.

(b) 611 mg of the sulphone-ester prepared above (1.3×10⁻³ mol) are run slowly into a solution of 436.8 mg of potassium t-butylate (3.9×10⁻³ mol) in 10.2 cm³ of tetrahydrofuran. The reaction mixture is kept for 17 hours at 20° C. in the absence of light and under an argon atmosphere and then it is poured rapidly into 200 cm³ of a 50/50 water/diethyl ether mixture. The ether portion is washed with 4 times 50 cm³ of water and then evaporated in vacuo. 436 mg of an orange-red oil are thus obtained, which, when dissolved in ethanol, gives an absorption maximum at 324 nm ($E_1\,_{cm}{}^{1\%}$=890) in UV spectrography, characteristic of vitamin A.

EXAMPLE 2

(a) 1.9 g of the sulphone-ester of the formula II prepared above, 893 mg of potassium hydroxide, 2 cm³ of water and 15 cm³ of absolute alcohol are introduced into a 30 cm³ flask. The reaction mixture is stirred for 15 hours at ambient temperature and then poured into 200 cm³ of water; it is extracted with 3 times 100 cm³ of diethyl ether. The product is washed with water, dried and then evaporated to remove the ether. 1.5 g. of a viscous red oil are thus obtained in which the desired sulphone-alcohol is measured by thin layer chromatography. The degree of conversion is 100% and the yield is 80%. Recrystallisation from methanol yields a white solid, of melting point 50°–51° C., which, from elementary analysis, infra-red spectrography and nuclear magnetic resonance, corresponds to the formula:

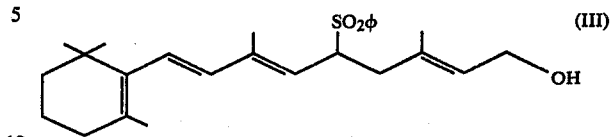
(III)

(b) 535 mg of the sulphone-alcohol obtained are run slowly into 436.8 mg of potassium t-butylate and 5 cm³ of pyridine. This mixture is treated under the conditions of the preceding Example under part (b) and 450 mg of an orange-red oil are thus obtained which, when dissolved in ethanol, gives an absorption maximum at 325 nm ($E_1\,_{cm}{}^{1\%}$=739) in UV spectrography, indicating the presence of vitamin A.

EXAMPLE 3

Following the procedure of Example 1, 23.9 g of phenyl-5-(2,6,6-trimethyl-cyclohex-1-enyl)-3-methyl-penta-2,4-dienyl-sulphone (6.9×10⁻² mol) are dissolved in 60 cm³ of tetrahydrofuran and this solution is run into a suspension of 15.6 g. of potassium t-butylate in 83 cm³ of tetrahydrofuran. The reaction mixture is left for 30 minutes at −30° C. and then 11.2 g of 1-chloro-2-methyl-4-methoxy-2-butene (8.4×10⁻² mol) dissolved in 20 cm³ of tetrahydrofuran are run in. The mixture is left for 2 hours at −30° C. and then the temperature is allowed to rise slowly to 23° C. The tetrahydrofuran is removed from the reaction mixture, which has become dark brown, by means of the vacuum provided by a water pump, 300 cm³ of water are added and the product is then extracted with 3 times 200 cm³ of diethyl ether. After washing with water, drying and concentration in vacuo, 32 g of an orange-yellow viscous oil are obtained. Analysis of this oil by thin layer chromatography indicates a degree of conversion of 100% of the starting sulphone and a yield of 85% of the desired product. Recrystallization of this oil from methanol yields a white solid product, of melting point 94° C., corresponding to the formula:

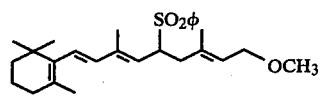
(IV)

When dissolved in ethanol, this product gives an absorption maximum at 271 nm ($E_1\,_{cm}{}^{1\%}$=484) in UV spectrography.

1-Chloro-2-methyl-4-methoxy-2-butene was prepared by reacting t-butyl hypochlorite with isoprene dissolved in methanol according to the process described in J. Am. Chem. Soc. 72, p. 4610 (1950).

By treating the sulphone-ether (IV) under the conditions of Example 2 under part (b) the methyl ether of vitamin A is obtained on desulphonation and is identified by its UV spectrum which, when dissolved in ethanol, gives an absorption maximum $E_1\,_{cm}{}^{1\%}$=648 at 325 mμ.

EXAMPLE 4

A solution of 3.44 g (1×10⁻² mol) of phenyl-5-(2,6,6-trimethyl-cyclohex-1-enyl)-3-methyl-penta-2,4-dienyl-sulphone in 7 cm³ of tetrahydrofuran is run into a suspension prepared from 4.6 g of potassium t-butylate and 10 cm³ of tetrahydrofuran which has been cooled to −50° C. A solution of 4.12 g of 1-bromo-2-methyl-4,4-diethoxy-2-butene in 10 cm³ of diethyl ether is then added. The mixture is kept at −50° C. for 30 minutes and then at −20° C. for 2 hours and thereafter at 0° for 3 hours. The reaction mixture is then poured into 50 cm³ of a 50/50 mixture of iced water and diethyl ether. It is extracted with 4 times 20 cm³ of diethyl ether and the ether layer is washed with an aqueous solution of potassium chloride, dried over magnesium sulphate and filtered and the ether is evaporated in vacuo. 6 g of a red oil are thus obtained in which 3.6 g of a sulphone, identified by infra-red spectrography and nuclear magnetic resonance, of the formula:

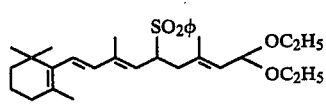
(V)

are measured by thin layer chromatography. The yield is 72%.

1-Bromo-2-methyl-4,4-diethoxy-2-butene was prepared by bromoethoxylation of 1-ethoxy-3-methyl-butadiene in accordance with the process described in Journal General Chemistry USSR 32 No. 4, 1091 (1962).

EXAMPLE 5

A solution of 3.44 g of phenyl-5-(2,6,6-trimethylcyclohex-1-enyl)-3-methyl-penta-2,4-dienyl-sulphone in 5 cm³ of anhydrous tetrahydrofuran is run into a suspension of 2 g of potassium t-butylate in 5 cm³ of tetrahydrofuran which has been cooled to −30° C. The mixture is stirred for 10 minutes at −30° C. and then a solution of 2.44 g of phenyl-4-chloro-3-methyl-but-2-enyl-sulphone in 15 cm³ of tetrahydrofuran is run in over the course of 7 minutes. The reaction mixture is left to react for 3 hours 30 minutes at −30° C. and is then poured into 50 cm³ of iced water. The mixture is extracted with 3 times 40 cm³ of diethyl ether and the combind ether layers are washed with 3 times 30 cm³ of water, dried over magnesium sulphate and filtered and the ether is evaporated from the filtrate. 5.8 g of a crude solid product, which contains 4.95 g of a disulphone, are thus obtained. The disulphone is recrystallized from a 50/50 diisopropyl ether/methanol mixture in the form of white crystals of melting point, (KOFLER) 123° C. It gives an absorption maximum at 236 nm ($E_1\ cm^{1\%}=295$) and at 268 nm ($E_1\ cm^{1\%}=260$) in hexane in UV spectrography and corresponds to the formula:

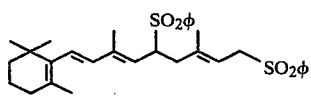
(VI)

The yield relative to the sulphone employed is 89.5%.

Phenyl-4-chloro-3-methyl-2-butene-sulphone was prepared by reacting sodium phenylsulphinate with 1,4-dichloro-2-methyl-2-butene in equimolecular amounts, in anhydrous ethanol, at a temperature of 38° C. for 15 hours. The heterogeneous mixture which is obtained is filtered and the filtrate is placed in the refrigerator overnight. A white crystalline precipitate is thus obtained, of melting point 88° C., which is phenyl-4-chloro-3-methyl-but-2-enylsulphone.

EXAMPLE 6

A solution of 2.05 g of phenyl-retinyl-sulphone in 6 cm³ of tetrahydrofuran is run, over the course of 6 minutes, into a suspension of 1.9 g of potassium t-butylate in 3 cm³ of tetrahydrofuran which has been cooled to 0° C. A solution of 0.980 g of 1-chloro-2-methyl-4-acetoxy-2-butene in 6 cm³ of anhydrous tetrahydrofuran is then run in over the course of 15 minutes and the mixture is stirred for 15 minutes at ambient temperature (18° C.) The reaction mixture is left for 3 hours at this temperature and then it is poured into a mixture of 80 cm³ of iced water and 40 cm³ of diethyl ether. The mixture is then decanted, the aqueous layer is extracted with 3 times 40 cm³ of diethyl ether and the ether layer is washed with water. By treating the ether layers as above, 1.8 g of a $C_{25}$ sulphone, of the formula:

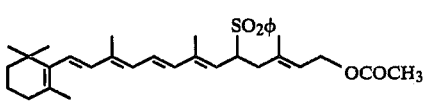
(VII)

are obtained. Yield 67.1% relative to the sulphone employed.

Preparation of phenyl-retinyl-sulphone: 1.43 g. of 9-(2,6,6-trimethyl-cyclohex-1-enyl)-3,7-dimethyl-nona-1,4,6,8-tetraen-3-ol or 3-retinol dissolved in 3 cm³ of ether are added to a solution of 1.06 g of sodium phenylsulphinate in 100 cm³ of acetic acid. The reaction mixture is left to stand for several hours and is then poured into 60 cm³ of water. The aqueous layer is extracted with 4 times 10 cm³ of diethyl ether. The ether layers are washed with an aqueous solution of sodium bicarbonate and then dried over magnesium sulphate. On evaporating the ether, phenyl-retinyl-sulphone is obtained.

EXAMPLE 7

Following the conditions of Example 5, 2.05 g of phenyl-retinyl-sulphone dissolved in 6 cm³ of tetrahydrofurane are reacted with 1.22 g of phenyl-4-chloro-3-methyl-but-2-enyl-sulphone dissolved in 6 cm³ of tetrahydrofurane, in the presence of 1.9 g of potassium t-butylate.

The reaction mixture is then poured into 80 cm³ of a 50/50 iced water/diethyl ether mixture. After decanting, washing the aqueous layer with ether and treating the combined ether layers, (drying, filtration, evaporation of the ether), 3.7 g of a yellow solid product, which contains 2.6 g of a disulphone identified by N.M.R. and I.R. and corresponding to the formula:

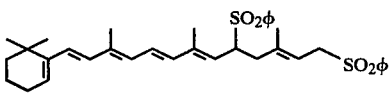
(VIII)

are obtained. The yield is 83.8% relative to the sulphone employed.

EXAMPLE 8

Following the same procedure as in the preceding Examples, 1.8 g of a sulphone corresponding to the formula:

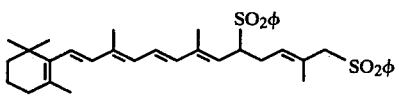

dissolved in 15 cm³ of tetrahydrofuran are reacted with 5-(2,6,6-trimethyl-cyclohex-1'-enyl)-3-methyl-1-chloropenta-2,4-diene dissolved in 20 cm³ of diethyl ether, in the presence of 3.75 g of potassium t-butylate. The reaction mixture is left for 3 hours at −30° C. and then for 16 hours at 0° C. and is then poured into a mixture of 100 cm³ of iced water and 50 cm³ of diethyl ether. The mixture is decanted and the aqueous layer is extracted with 3 times 50 cm³ of diethyl ether. The combined ether layers are washed with water, dried over magnesium sulphate and then concentrated in vacuo. 3.85 g of an orange product are thus obtained in which 1.35 g of a disulphone corresponding to the formula:

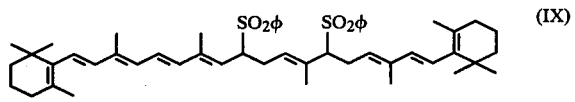

are identified and measured.

When this disulphone of the formula (IX) is desulphonated by an alkaline agent it is converted into β-carotene.

5-(2,6,6-Trimethyl-cyclohex-1-enyl)-3-methyl-1-chloro-penta-2,4-diene is obtained by reacting phosphorus trichloride with vinyl β-ionol, according to a known process.

The starting C₂₅ disulphone is described and claimed in U.S. Ser. No. 328,624 filed Feb. 1, 1973, in the name of the applicants. It was prepared in the following manner: 2.05 g of phenyl-retinyl-sulphone (the preparation of which is given in Example 6) in 6 cm³ of tetrahydrofuran, followed by 1.22 g of phenyl-4-chloro-2-methyl-but-2-enyl-sulphone in 5 cm³ of the same solvent, are added to a solution of 1.88 g of potassium t-butylate in 3 cm³ of tetrahydrofuran which has been cooled to −25° C. The temperature is then kept at −15° C. for 7 hours 30 minutes. After having kept the reaction mixture at −70° C. for 16 hours, it is poured into a mixture of 80 cm³ of water and 50 cm³ of diethyl ether. The C₂₅ disulphone is isolated from the ether layers by evaporating the solvent.

Phenyl-4-chloro-2-methyl-but-2-enyl-sulphone was prepared by reacting phenylsulphonyl chloride with isoprene in accordance with the process described in French Pat. No. 1,409,516.

EXAMPLE 9

3.36 g of potassium t-butylate and 25 cm³ of tetrahydrofuran are introduced into a flask and are cooled, under argon, to −20° C. A solution of 2.1 g of prenyl-phenylsulphone in 7 cm³ of tetrahydrofuran is then run in, whilst maintaining the same temperature. A solution of 1.95 g of 1-chloro-2-methyl-4-acetoxy-2-butene in 5 cm³ of tetrahydrofuran is then also run in over the course of 15 minutes. The mixture is kept at −20° C., with stirring, for 2 hours 20 minutes and then the temperature is allowed to rise to +20° C. over the course of 45 minutes. After removing the solvent by applying a vacuum 0.56 g of potassium hydroxide dissolved in 15 cm³ of ethanol and 2 cm³ of water is added. The reaction mixture is stirred for 1 hour at 35° C. and is then poured into a mixture of 300 cm³ of water and 150 cm³ of diethyl ether. The combined ether layers are dried over magnesium sulphate and then concentrated, and from them 2.9 grams of an orange-yellow oil are isolated which is identified by nuclear magnetic resonance and I.R. spectrography, as being a compound corresponding to the formula:

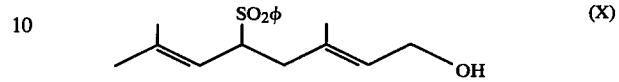

The yield is 78% relative to the prenyl-phenyl-sulphone.

The sulphone of the formula X can be converted into geraniol: to do this, 1.48 g of this sulphone and 50 cm³ of ethylamine are introduced into a 100 cm³ flask and the temperature is adjusted to approximately 5° to 10° C. 0.347 g of lithium is added in small portions and the reaction mixture is stirred for 2 hours 15 minutes. 1.5 g. of ammonium chloride are then added and the ethylamine is then driven off by heating at 30° C. under a stream of argon and 50 cm³ of water and 30 cm³ of diethyl ether are added. The aqueous layer is decanted and extracted with 3 times 50 cm³ of diethyl ether; the combined ether layers are washed with water, dried over magnesium sulphate and then concentrated in vacuo. 640 mg of a pale yellow oil are thus isolated in which geraniol is characterised and measured by infrared spectography and nuclear magnetic resonance. The yield of geraniol is 85% relative to the starting sulphone.

Prenyl-phenyl-sulphone, used to prepare the sulphone of the formula IX, was prepared from prenyl chloride and sodium phenylsulphinate in accordance with the usual method for preparing sulphones employing an alkali sulphinate.

EXAMPLE 10

2.24 g of potassium t-butylate in 20 cm³ of tetrahydrofuran are added to a solution of 2.3 g of geranyl bromide in 15 cm³ of tetrahydrofuran, keeping the temperature at −50° C. A solution of 3.12 g of phenyl-4-methoxy-2-methyl-but-2-enyl-sulphone in 15 cm³ of tetrahydrofuran is then run in over the course of 30 minutes.

The reaction mixture is kept under these conditions for 2 hours 15 minutes and is then poured into a mixture of 250 cm³ of water and 100 cm³ of diethyl ether. After decanting and extracting the aqueous layer with 3 times 50 cm³ of diethyl ether, the combined ether layers are washed with water, dried over magnesium sulphate and concentrated by evaporation. 4.53 g of an orange-brown oil are thus obtained in which the compound of the formula:

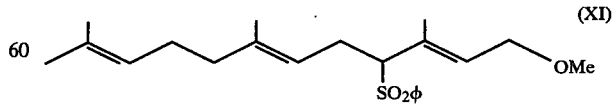

is identified and measured by thin layer chromatography and nuclear magnetic resonance.

The degree of conversion of the sulphone employed is 60% and the yield of the compound of the formula XI is 84%.

Phenyl-4-methoxy-2-methyl-but-2-enyl-sulphone was prepared by reacting sodium phenylsulphinate with 4-methoxy-2-methyl-but-2-enyl bromide, in a solvent medium such as ethylene glycol, by heating at 100° C. for 2 hours.

EXAMPLE 11

(a) 3.68 g of potassium t-butylate and 5 cm³ of tetrahydrofuran are introduced into a flask which is cooled to −40° C., and then 3.1 g of phenyl-5-(2,6,6-trimethyl-cyclohex-1-enyl)-3-methyl-penta-2.4-dienyl-sulphone dissolved in 4 cm³ of tetrahydrofuran are run in over the course of 5 minutes. 3 cm³ of tetrahydrofuran containing 3.1 g of 13-(2,6,6-trimethyl-cyclohex-1-enyl)-5-phenylsulphonyl-2,7,11-trimethyl-1-chloro-trideca-2,6,8,10,12-pentaene (a chlorinated C$_{25}$ sulphone) are then run in over the course of 10 minutes. The temperature is kept between −40° C. and −50° C. for 5 hours. The reaction mixture is then poured into a mixture of 25 cm³ of iced water and 25 cm³ of diethyl ether and then treated as in the preceding examples. 9.8 g of a yellow solid product are obtained in which 2.87 g of a compound corresponding to the formula:

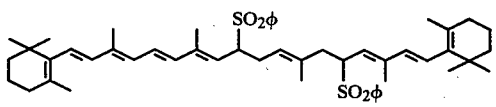

are identified and measured.

Yield 49% relative to the chlorinated sulphone.

The chlorinated C$_{25}$ sulphone was prepared by reacting phenyl-retinyl-sulphone dissolved in tetrahydrofurane with 1,4-dichloro-2-methyl-2-butene in this same solvent, in the presence of potassium t-butylate in tetrahydrofurane. The temperature is kept at −70° C. for 7 hours.

(b) Preparation of β-carotene: 1.43 g of the compound of the formula XII, 4.5 g of potassium t-butylate and 25 cm³ of anhydrous pyridine are introduced into a flask. The mixture is heated for 3 hours at 50°–55° C. and then left to stand overnight at a temperature of 20°–21° C.

The mixture is acidified to pH 5 by means of a normal aqueous solution of sulphuric acid and then concentrated by evaporation without exceeding 40° C. in the mixture. The residue is taken up in a mixture of 50 cm³ of water and 50 cm³ of diethyl ether and the aqueous layer is decanted and then extracted with diethyl ether. The combined ether layers are treated as in the preceding examples. A dark red solid product which contains 0.61 g of β-carotene is isolated. Yield 65.5% relative to the product of the formula XII.

EXAMPLE 12

4.1 g of 75% pure farnesyl bromide are dissolved in 15 cm³ of tetrahydrofuran; the solution is cooled to −50° C. and 2.24 g of potassium t-butylate in 20 cm³ of tetrahydrofuran are added. A solution of 3.12 g of 4-methoxy-2-methyl-but-2-enyl-phenyl-sulphone in 15 cm³ of tetrahydrofuran is then added. The reaction mixture is kept at −50° C. for 2 hours 15 minutes and is then poured into a mixture of 250 cm³ of water+100 cm³ of diethyl ether. The ether layers are washed with water, dried, filtered and concentrated. 6.35 g of an orange-yellow oil are thus obtained in which a compound corresponding to the formula:

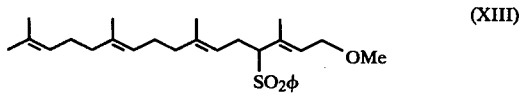

is identified and measured by thin layer chromatography and nuclear magnetic resonance.

The degree of conversion of the C$_5$ sulphone is 60%. The yield of the compound XIII relative to this sulphone is 86%.

EXAMPLE 13

A solution of 3.47 g of phenyl-farnesyl-sulphone in 15 cm³ of tetrahydrofuran is run into 20 cm³ of this same solvent which contains 2.24 g of potassium t-butylate and which is cooled to −30° C. A solution of 1.93 g of methyl bromo-senecioate in 15 cm³ of tetrahydrofuran is then run in over the course of 40 minutes. The compound corresponding to the formula:

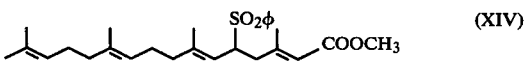

is identified by thin layer chromatography of the reaction mixture, 10 minutes after the addition of the bromo-senecioate is complete.

The mixture is kept at −30° C. and is stirred for 2 hours and is then poured into a mixture of 200 cm³ of water and 100 cm³ of diethyl ether. The ether layer is decanted and treated as in the preceding examples to yield 4.17 g of an orange oil in which methyl 2,6,10,14-tetramethyl-pentadeca-1,3,5,9,13-pentaene-carboxylate is characterised and measured by nuclear magnetic resonance.

Degree of conversion of the starting sulphone: 100%. Yield: 28%.

EXAMPLE 14

3.44 g of the C$_{15}$ phenyl-sulphone used in Example 1 are dissolved in 10 cm³ of tetrahydrofuran and the solution is run into 12 cm³ of tetrahydrofuran which contains 2.24 g of potassium t-butylate and which has been cooled to −30° C. A solution of 0.347 g of 1,4-dichloro-2-methyl-2-butene in 5 cm³ of tetrahydrofuran is then run in over the course of 15 minutes. By a treatment identical to that of the preceding Examples, 3.9 g of a product which contains 1.4 g of the compound of the formula:

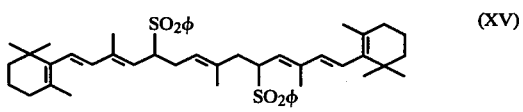

are isolated.

Yield 73% relative to the dichlorinated product.

EXAMPLE 15

A mixture of 1.88 g of potassium t-butylate and 3 cm³ of tetrahydrofuran is cooled to −70° under an atmosphere of nitrogen. A solution of 3.1 g of the disulphone of the formula:

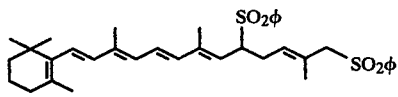

in 15 cm³ of tetrahydrofuran is run in first over the course of 10 minutes, followed by a solution of 1.94 g of 1-chloro-3-methyl-4-t-butoxy-2-butene in 3 cm³ of tetrahydrofuran. Stirring is continued at this temperature for 19 hours. The reaction mixture is poured into a water/diethyl ether mixture and treated according to the preceding examples. An orange-red oil, which contains 2.4 g of a compound of the formula

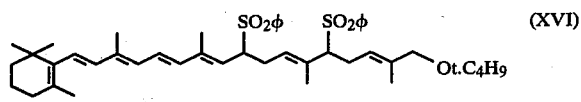

is thus obtained.

Yield of 72% relative to the disulphone employed.

The disulphone employed was prepared by reacting phenyl-retinyl-sulphone with phenyl-4-chloro-2-methyl-but-2-enyl-sulphone in tetrahydrofuran and in the presence of potassium t-butylate at −15° C. or as described in Example 8.

EXAMPLE 16

7.5 cm³ of a solution of butyl-lithium in hexane (obtained by dissolving 17 g of this product in 100 cm³ of hexane) which has been cooled to −70° C., are added to 4 g of phenyl-3-methyl-but-2-enyl-sulphone and the mixture is stirred for 1 hour. 3.86 g of methyl bromo-senecioate dissolved in 20 cm³ of tetrahydrofuran cooled to −70° C. are then added and stirring is continued for 1 hour whilst allowing the mixture to return to ambient temperature. It is poured into 100 cm³ of a saturated aqueous solution of sodium chloride mixed with 100 cm³ of an aqueous solution of sodium bicarbonate. It is then extracted with 3 times 100 cm³ of diethyl ether. A residue which crystallises on adding pentane and has a melting point of 42°–43° C. is isolated from the ether layers, treated as above. This product is identified by elementary analysis, infra-red spectrography and nuclear magnetic resonance and corresponds to the formula:

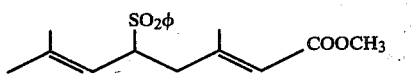

Yield 83% relative to the sulphone employed.

EXAMPLE 17

Following the procedure of the preceding example, 4.4 g of phenyl-3-methyl-but-2-enyl-sulphone are reacted with 4.55 g of 1-chloro-2-methyl-4-acetoxy-2-butene. At the end of the treatment, a product is isolated which is identified by elementary analysis, infra-red spectrography and nuclear magnetic resonance and corresponds to the formula:

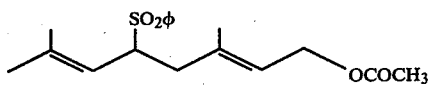

The yield is 73% relative to the sulphone employed.

EXAMPLE 18

1.3 g of potassium methylate, 10 cm³ of hexamethyl-phosphotriamide and 10 cm³ of diethyl ether are introduced into a 50 cm³ flask. The mixture is cooled to −20° C. and then a solution of 2.05 g of phenyl-retinyl-sulphone in a mixture of 5 cm³ of hexamethyl-phosphotriamide and 5 cm³ of anhydrous diethyl ether is added slowly. A solution of 1.93 g of methyl bromo-senecioate in 3 cm³ of anhydrous diethyl ether is then run in over the course of 10 minutes and stirring is continued for 2 hours 30 minutes at −20° C. The reaction mixture is poured into a mixture of 50 cm³ of iced water and 50 cm³ of diethyl ether and then the ether layers are treated as in the preceding examples. An orange viscous product is obtained in which 1.85 g of a product of the formula:

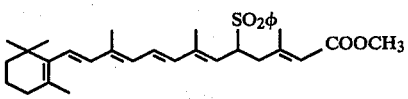

are measured.

Yield: 71% relative to the sulphone employed.

EXAMPLE 19

A solution of 4.31 g of 5-(2,6,6-trimethyl-3-oxocyclohex-1-enyl)-3-methyl-1-phenylsulphonyl-penta-2,4-diene in 20 cm³ of acetonitrile, followed by 0.2 g of trimethyl-benzyl-ammonium hydroxide (TRITON B) dissolved in 3 cm³ of acetonitrile, are introduced into a 50 cm³ three-necked flask equipped with a dropping funnel, a condenser and a nitrogen inlet. A solution of 2.1 g of 1-phenylsulphonyl-3-methyl-butadiene in 10 cm³ of acetonitrile is then run into the flask, over the course of 10 minutes. The reaction mixture is stirred for several hours at ambient temperature and is then poured into a mixture of 200 cm³ of water and 100 cm³ of diethyl ether. The aqueous layer is decanted and extracted with 3 times 100 cm³ of diethyl ether; the combined ether layers are washed with 3 times 100 cm³ of water, dried over magnesium sulphate and concentrated. 6.1 g of an oil are thus obtained in which a product of the formula:

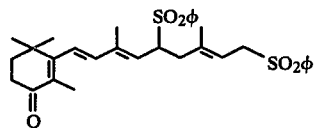

is identified and measured by infra-red spectrography, nuclear magnetic resonance and thin layer chromatography.

Degree of conversion: 61%. Yield: 54%.

5-(2,6,6-trimethyl-3-oxo-cyclohex-1-enyl)-3-methyl-1-phenylsulphonyl-penta-2,4-diene was prepared by oxidation of 5-(2,6,6-trimethyl-cyclohex-1-enyl)-3-methyl-1-phenyl-sulphonyl-penta-2,4-diene by means of sodium meta-periodate in accordance with the process described in French Pat. No. 2,071,508. The product oxidised in this way was itself obtained by reacting sodium phenylsulphinate with 5-(2,6,6-trimethyl-cyclohex-1-enyl)-3-methyl-1-chloro-penta-2,4-diene as described in Example 1.

1-Phenylsulphonyl-3-methyl-butadiene was prepared by reacting phenyl-4-chloro-3-methyl-but-2-enylsulphone with triethylamine in benzene. The chlorosulphone which was dehydrochlorinated in this way was itself prepared by reacting sodium phenylsulphinate with 1,4-dichloro-2-methyl-2-butene in equimolecular amounts in anhydrous ethanol.

EXAMPLE 20

A solution of 2.257 g of tolyl-5-(2,6,6-trimethylcyclohex-1-enyl)-3-methyl-penta-2,4-dienyl sulphone in 3.5 cm$^3$ of N-methylpyrrolidone is added with agitation and over a period of 5 minutes to a solution of 0.886 g of sodium t-butylate in 3 cm$^3$ of N-methylpyrrolidone maintained under argon and cooled to −20° C. The reaction mixture turns red. After 5 minutes agitation, a solution of 1.4105 g of 1-chloro-2-methyl-4,4-dimethoxy-2-butene in 1.7 cm$^3$ of N-methyl-pyrrolidone is added over 5 minutes. The reaction is followed by thin layer chromatography using as eluent a mixture of hexane, diethyl ether and ethanol (70/25/5 by volume). After 42 minutes the sulphone starting material has entirely reacted. 6 cm$^3$ of N-methylpyrrolidone are added and the pH of the mixture is adjusted to about 6 by addition of 0.74 cm$^3$ of 4 N-sulphuric acid. A further 0.16 cm$^3$ of 4 N-sulphuric acid is then added, and the mixture is then allowed to warm up slowly to about 20° C. while the hydrolysis of the acetal group is followed by thin layer chromatography using the same eluent as before. After 65 minutes, the reaction mixture is diluted with 25 cm$^3$ of diethyl ether and 10 cm$^3$ of distilled water. The aqueous phase is separated and extracted with more ether. The ethereal extracts are united and washed with distilled water until the pH of the washing water is about 6. The extract is then dried over anhydrous sodium sulphate and concentrated. 3.00 g of 9-(2,6,6-trimethylcyclohex-1-enyl)-5-tolylsulphonyl-3,7-dimethyl-2,6,8-nona-trienone melting at 97° C. are thus obtained after recrystallisation from a mixture of hexane and ethyl acetate (80/20 by volume). This compound shows by ultra-violet spectroscopy in solution in ethanol an absorption maximum at 233 nm and a shoulder at 272 nm. It has the formula:

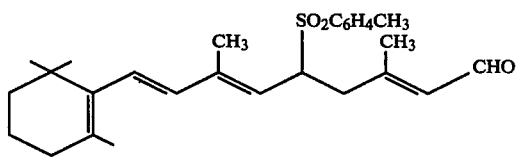

EXAMPLE 21

A solution of 3.501 g of (4-methoxyphenyl)-5-(2,6,6-trimethylcyclohex-1-enyl)-3-methyl-penta-2,4-dienyl sulphone in 3.6 cm$^3$ of N-methylpyrrolidone is added with agitation and over a period of 10 minutes to a solution of 1.165 g of sodium t-butylate in 3 cm$^3$ of N-methylpyrrolidone maintained under argon and cooled to −20° C. The addition causes the reaction mixture to turn red. After 5 minutes agitation, a solution of 1.664 g of 1-chloro-2-methyl-4,4-dimethoxy-2-butene in 1.7 cm$^3$ of N-methylpyrrolidone are added over a period of 5 minutes. The reaction is followed by thin layer chromatography using the same eluent as in Example 20. After 90 minutes, the sulphone starting material has entirely reacted. 6 cm$^3$ of N-methylpyrrolidone are added, and the pH of the mixture is adjusted to about 6 by addition of 0.74 cm$^3$ of 4 N-sulphuric acid. A further 0.23 cm$^3$ of 4 N-sulphuric acid is then added and the temperature of the mixture is allowed to rise progressively to about 20° C., while the hydrolysis of the acetal group is followed by thin layer chromatography using the same eluent as before. After 2 hours, 25 cm$^3$ of diethyl ether and 10 cm$^3$ of distilled water are added to the reaction mixture, and the aqueous phase is separated and extracted with more ether. The ethereal extracts are combined and washed with distilled water until the pH of the washing water is about 6. The extract is then dried over anhydrous sodium sulphate and concentrated. 3.4 g of 9-(2,6,6-trimethylcyclohex-1-enyl)-5-(4-methoxyphenylsulphonyl)-3,7-dimethyl-2,6,8-nona-trienone are thus obtained, which shows by ultraviolet spectroscopy in solution in ethanol an absorption maximum at 242 nm and a shoulder at 272 nm.

EXAMPLE 22

A solution of 3.501 g of (4-chlorophenyl)-5-(2,6,6-trimethylcyclohex-1-enyl)-3-methyl-penta-2,4-dienyl sulphone in 5 cm$^3$ of N-methylpyrrolidone is added with agitation and over 5 minutes to a solution of 1.169 g of sodium t-butylate in 4 cm$^3$ of N-methylpyrrolidone kept under nitrogen and cooled to −20° C. The addition causes the reaction mixture to turn red. After 5 minutes agitation, a solution of 1.664 g of 1-chloro-2-methyl-4,4-dimethoxy-2-butene in 2.25 cm$^3$ of N-methyl-pyrrolidone is added over 5 minutes. The reaction is followed by thin layer chromatography using the same eluent as in Example 20. After 1 hour and 47 minutes the sulphone starting material has entirely reacted. 8 cm$^3$ of N-methylpyrrolidone are added, and the pH of the mixture is adjusted to about 6 by addition of 0.77 cm$^3$ of 4 N-sulphuric acid. A further 0.22 cm$^3$ of 4 N-sulphuric acid is then added, and the temperature of the mixture is allowed to rise progressively to about 20° C. while the hydrolysis of the acetal group is followed by thin layer chromatography using the same eluent as before. After 2 hours, 25 cm$^3$ of diethyl ether and 10 cm$^3$ of distilled water are added to the reaction mixture. The aqueous phase is separated and extracted with more ether. The ethereal extracts are combined and washed with distilled water until the pH of the washing water is about 6. The extract is then dried with anhydrous sodium sulphate and concentrated. 4.4 g of 9-(2,6,6-trimethylcyclohex-1-enyl)-5-(4-chlorophenylsulphonyl)-3,7-dimethyl-2,6,8-nona-trienone, melting at 125° C. after recrystallisation from a mixture of hexane and ethyl acetate (80/20 by volume), are thus obtained showing, on ultraviolet spectroscopy in solution in ethanol, an absorption maximum at 232 nm and a shoulder at 272 nm.

EXAMPLE 23

A solution of 2.786 g of (2,5-dichlorophenyl)-5-(2,6,6-trimethylcyclohex-1-enyl)-3-methyl-penta-2,4-dienylsulphone in 3.6 cm$^3$ of N-methylpyrrolidone is added with agitation and over a period of 5 minutes to a solution of 0.834 g of sodium t-butylate in 2.9 cm$^3$ of N-methylpyrrolidone kept under argon and cooled to −20° C. The addition causes the reaction mixture to turn red. After 5 minutes agitation, a solution of 1.1909 g of 1-chloro-2-methyl-4,4-dimethoxy-2-butene in 1.3 cm$^3$ of N-methylpyrrolidone is added over 5 minutes. The reaction is followed by thin layer chromatography using the same eluent as in Example 20. After 1 hour and a half the sulphone starting material has entirely reacted. 6 cm³ of N-methylpyrrolidone are added, and the pH of the mixture is adjusted to about 6 by addition of 0.52 cm³ of 4 N-sulphuric acid. A further 0.26 cm³ of 4 N-sulphuric acid is added and the temperature of the mixture is allowed to rise progressively to about 20° C. while the hydrolysis of the acetal group is followed by thin layer chromatography using the same eluent as before. After 2 hours, 25 cm³ of diethyl ether and 10 cm³ of distilled water are added to the reaction mixture, and the aqueous phase is separated and extracted with more ether. The ethereal extracts are combined, washed with water until the washings have a pH of about 6, and then dried over anhydrous sodium sulphate and concentrated. 3 g of 9-(2,6,6-trimethylcyclohex-1-enyl)-5-(2,-5-dichlorophenylsulphonyl)-3,7-dimethyl-2,6,8-nona-trienone, melting at 122° C. after recrystallisation from a mixture of hexane and ethyl acetate (80/20 by volume) are thus obtained, showing on ultraviolet spectroscopy in solution in ethanol absorption maxima at 233 nm and 283 nm.

EXAMPLE 24

A solution of 7.98 g of (2-naphthyl)-5-(2,6,6-trimethyl-cyclohex-1-enyl)-3-methyl-penta-2,4-dienyl sulphone in 16 cm³ of N-methylpyrrolidone is added with agitation and over a period of 5 minutes to a solution of 2.54 g of sodium t-butylate in 8.5 cm³ of N-methylpyrrolidone kept under argon and cooled to −20° C. The addition causes the reaction mixture to turn maroon-coloured. After 5 minutes agitation, a solution of 3.9 g of 1-chloro-2-methyl-4,4-dimethoxy-2-butene in 5 cm³ of N-methylpyrrolidone is added over 5 minutes. The reaction is followed by thin layer chromatography using the same eluent as in Example 20. After 1 hour and a half, the sulphone starting material has entirely reacted. 11.5 cm³ of N-methylpyrrolidone are added, and the pH of the mixture is adjusted to about 7 by addition of 1.6 cm³ of 4 N-sulphuric acid. A further 0.5 cm³ of 4 N-sulphuric acid is then added, and the temperature of the mixture is allowed to rise progressively to about 20° C. while the hydrolysis of the acetal group is followed by thin layer chromatography using the same eluent as before. After 2 hours, 25 cm³ of diethyl ether and 5 cm³ of distilled water are added to the reaction mixture. The aqueous phase is separated, and extracted with ether. The ethereal extracts are combined, washed with distilled water until the pH of the washings is about 6, dried over anhydrous sodium sulphate, and concentrated. 9.72 g of 9-(2,6,6-trimethylcyclohex-1-enyl)-5-(2-naphthylsulphonyl)-3,7-dimethyl-2,6,8-nona-trienone melting at 124° C. after recrystallisation from a mixture of hexane and ethyl acetate (80/20 by volume) are thus obtained showing, on ultraviolet spectroscopy in solution in ethanol, an absorption maximum at 230 nm and a shoulder between 270 and 280 nm.

EXAMPLE 25

A solution of 8.51 g of (4-bromophenyl)-5-(2,6,6-trimethylcyclohex-1-enyl)-3-methyl-penta-2,4-dienyl sulphone in 16 cm³ of N-methylpyrrolidone is added with stirring over a period of 5 minutes to a solution of 2.54 g of sodium t-butylate in 8.5 cm³ of N-methylpyrrolidone kept under argon and cooled to −20° C. The reaction mixture turns red. After 10 minutes stirring, a solution of 3.9 g of 1-chloro-2-methyl-4,4-dimethoxy-2-butene in 4 cm³ of N-methylpyrrolidone is added over a period of 10 minutes. The reaction is followed by thin layer chromatography using as eluent a mixture of hexane, diethyl ether and ethanol (70:25:5 by volume). After 30 minutes, the sulphone starting material has entirely reacted. 11.5 cm³ of N-methylpyrrolidone are added, the pH of the mixture is adusted to about 6 by addition of 1.6 cm³ of 4 N-sulphuric acid, and a further 0.5 cm³ of 4 N-sulphuric acid is added. The temperature is allowed to rise progressively to about 20° C., while the hydrolysis of the acetal group is followed by thin layer chromatography using the same eluent as before. After 50 minutes, the reaction mixture is mixed with 25 cm³ of diethyl ether and 40 cm³ of distilled water. The aqueous phase is separated and extracted with more ether. the ethereal extracts are combined, washed with distilled water until the pH of the washing water is about 6, dried over anhydrous sodium sulphate, and concentrated. 11.5 g of 9-(2,6,6-trimethylcyclohex-1-enyl)-5-(4-bromophenylsulphonyl)-3,7-dimethyl-2,6,8-nona-trienone are thus obtained, m.p. 128° C. after recrystallisation from a mixture of hexane and ethyl acetate (80:20 by volume) and showing by ultra-violet spectrography in solution in ethanol an absorption maximum at 238 nm and a shoulder at 274 nm.

EXAMPLE 26

A solution of 7.24 g of (4-fluorophenyl)-5-(2,6,6-trimethylcyclohex-1-enyl)-3-methyl-penta-2,4-dienyl sulphone in 16 cm³ of N-methylpyrrolidone is added with stirring and over 20 minutes to a solution of 2.54 g of sodium t-butylate in 8.5 cm³ of N-methylpyrrolidone kept under argon and cooled to −20° C. The reaction mixture turns a maroon colour. After 10 minutes stirring, a solution of 3.9 g of 1-chloro-2-methyl-4,4-dimethoxy-2-butene in 5 cm³ of N-methylpyrrlidone is added over a period of 10 minutes. The reaction is followed by thin layer chromatography using an eluent a mixture of hexane, diethyl ether and ethanol (70:25:5 by volume). After 35 minutes, the sulphone starting material has entirely reacted. 11.5 cm³ of N-methylpyrrolidone are added, the pH of the mixture is adjusted to about 6 by addition of 1.6 cm³ of 4 N-sulphuric acid, and a further 0.5 cm³ of 4 N-sulphuric acid is added. The temperature is allowed to rise progressively to about 20° C., while the hydrolysis of the acetal group is followed by thin layer chromatography using the same eluent as before. After 1 hour 40 minutes the reaction mixture is mixed with 25 cm³ of diethyl ether and 40 cm³ distilled water. The aqueous phase is separated and extracted with ether. The ethereal extracts are combined, washed with distilled water until the pH of the washing water is about 6, dried over anhydrous sodium sulphate, and concentrated. 7.14 g of 9-(2,6,6-trimethylcyclohex-1-enyl)-5-(4-fluorophenylsulphonyl)-3,7-dimethyl-2,6,8-nona-trienone are thus obtained, m.p. 114° C. after recrystallisation from a mixture of hexane and ethyl acetate (80:20 by volume) and showing by ultra-violet spectrography in solution in ethanol an absorption maximum at 236 nm and a shoulder at 276 nm.

We claim:

1. A sulfone of the formula:

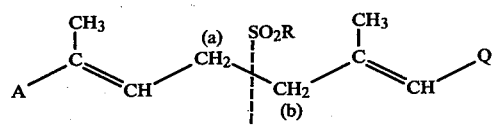

wherein A represents 2-(2,6,6-trimethyl-cyclohex-1-enyl)-ethenyl, R is an aryl radical substituted with a fluorine atom, a bromine atom, or an alkoxy group, and the sulfonyl group —SO$_2$R replaces a hydrogen atom on carbon (a) or (b), and Q is an etherified primary alcohol group —CH$_2$OH, or the primary alcohol group —CH$_2$OH, or a free aldehyde group or an acetal group, or the sulfonyl group —SO$_2$R replaces a hydrogen atom on carbon atom (a) and Q is an esterified primary alcohol group —CH$_2$OH.

2. 9-(2,6,6,-Trimethylcyclohex-1-enyl)-5-(4-methoxyphenylsulphonyl)-3,7-dimethyl-2,6,8-nona-trienone.

3. 9-(2,6,6-Trimethylcyclohex-1-enyl)-5-(4-bromophenylsulphonyl)-3,7-dimethyl-2,6,8-nona-trienone.

4. 9-(2,6,6-Trimethylcyclohex-1-enyl)-5-(4-fluorophenylsulphonyl)-3,7-dimethyl-2,6,8-nona-trienone.

5. A sulphone according to claim 1 wherein Q is a primary alcohol group or an alkyl ether group thereof containing a total of 2 to 7 carbon atoms or when the group —SO$_2$R replaces a hydrogen atom on carbon atom (a) Q is a primary alcohol group —CH$_2$OH esterified by an alkanoic acid of 1 to 6 carbon atoms.

* * * * *